(12) United States Patent
Nenno et al.

(10) Patent No.: US 8,212,553 B2
(45) Date of Patent: Jul. 3, 2012

(54) INSPECTION MODE SWITCHING CIRCUIT

(75) Inventors: Thomas W. Nenno, Murrysville, PA (US); Warren R. Junker, Monroeville, PA (US); Richard M. Novotny, New Kensington, PA (US); Conrad S. Wyffels, New Ulm, MN (US)

(73) Assignee: Westinghouse Electric Company LLC, Cranberry Township, PA (US)

( * ) Notice: Subject to any disclaimer, the term of this patent is extended or adjusted under 35 U.S.C. 154(b) by 295 days.

(21) Appl. No.: 12/642,935

(22) Filed: Dec. 21, 2009

(65) Prior Publication Data

US 2011/0148402 A1  Jun. 23, 2011

(51) Int. Cl.
  *G01N 27/82* (2006.01)
(52) U.S. Cl. ........ 324/240; 324/220; 324/222; 324/242; 324/339; 324/755.01; 324/239; 324/241

(58) Field of Classification Search .................. 324/239, 324/220, 222, 242, 339, 755.01, 240
See application file for complete search history.

(56) References Cited

U.S. PATENT DOCUMENTS

2004/0257072 A1* 12/2004 Samson .................. 324/242
2010/0079157 A1* 4/2010 Wincheski et al. ........... 324/699

* cited by examiner

*Primary Examiner* — Bot LeDynh
*Assistant Examiner* — Son Le

(57) ABSTRACT

An eddy current probe testing apparatus structured to operate concurrently in a driver pick-up mode and said impedance mode is provided. The eddy current probe has two coils. The eddy current probe testing apparatus also includes a signal producing device, an output device, and a switch assembly. The switch assembly is structured to switch how an input signal from the signal producing device is provided to the two coils.

14 Claims, 4 Drawing Sheets

INSPECTION MODE SWITCHING CIRCUIT

BACKGROUND OF THE INVENTION

1. Field of the Invention

The present invention relates to a robotic arm end effector having an eddy current detector and, more specifically, to a mode switching circuit that allows a robotic arm end effector having an eddy current detector to operate in two modes concurrently.

2. Related Art

Because of the radiation hazard present within the pressurized water vessel of a nuclear reactor, maintenance and testing of components within the pressurized water vessel are typically performed by remote service devices, such as robotic arms. Such a service device typically includes a robotic arm which can generally access any point within the pressure vessel. The robotic arm will be fitted with an end effector capable of performing specific maintenance or testing tasks. For example, the water inlet and outlet of the nuclear reactor pressure vessel must be inspected, inter alia, for surface and near surface defects. Such inspections are performed utilizing a "sled" coupled to the robotic arm.

The sled has a frame to which inspection devices may be coupled. Inspection devices typically include ultrasonic probes and eddy current probes. Ultrasonic probes emit and/or receive ultrasonic frequencies. Thus, the ultrasonic probes send an ultrasonic pulse and are structured to detect the reflection thereof. That is, the ultrasonic pulse will reflect differently at a defect than at a generally smooth surface. Eddy current probes operate by detecting changes in a magnetic field. That is, an eddy current probe has at least one electrical coil therein. When a signal, i.e. an alternating current, is passed through the coil(s), the coil(s) create a magnetic field. When the eddy current probe is placed adjacent to a conductive surface, the magnetic field interacts with the surface to create circulating eddy currents in the surface. If the surface is generally smooth, the eddy currents may be likened to the circular ripples in a pond after a rock has been dropped in the pond. The eddy currents, however, are generated repeatedly, and cyclically, so long as the signal is provided to the eddy current probe. More specifically, the characteristics of the eddy currents are tied to the characteristics, e.g. frequency, magnitude, phase, etc., of the signal. When there is a defect in the surface or near the surface (hereinafter "at" the surface), the pattern of the eddy currents on the surface is disturbed. By measuring the characteristics of the disturbed eddy current waves, the nature of the defect may be determined.

One type of eddy current probe is identified as a "+Point Probe," or a "X coil probe." A "+Point Probe" includes two conductive coils disposed in two generally perpendicular planes within a probe body (thus the "+" or the "X" in the name). Another type of eddy current probe is identified, colloquially, as a "pancake" probe wherein the two coils are stacked on top of each other, or where coils are disposed side-by-side. Of these configurations, the "+Point Probe" is preferred. The "+Point Probe" may be used in one of two modes; a "driver pick-up" mode and an "impedance" mode. In both modes the probe is used to create the eddy currents and to detect disturbances therein. By way of analogy, this is similar to shining a flashlight on a sheet of aluminum foil; where the foil is smooth, the light reflects without disturbance, but, where there is a crease, the light is distorted. In the disclosed method, however, the eddy current probe acts as both the flashlight, creating the light/electromagnetic waves, and the eyes, detecting the defect.

In the driver pick-up mode, the input signal is applied to one of the two coils. This coil creates a magnetic field which, in turn, produces eddy currents in an adjacent surface. The eddy currents also create a magnetic field which may effect the second coil. More specifically, a generally defect free surface will not produce a significant response in the second coil. If a defect exists at the surface, however, an abnormal magnetic field is created and can be detected by the second coil. Due to the interplay between the magnetic fields, in this configuration, the eddy current probe has a greater sensitivity to defects that extend at an angle to the planes of the coils.

In the impedance mode a signal is applied to both coils. Each coil creates a magnetic field and those magnetic fields create eddy currents in an adjacent surface. Further, the impedance created in each coil may be compared to the impedance in the other coil. When the probe is disposed over a generally defect free surface, the impedance in both coils is substantially the same. That is, where there is no defect, the field created by the eddy currents are substantially constant, therefore there is an equal feedback to both coils. A defect, however, disturbs the magnetic field created by the eddy currents and creates more impedance in one of the two coils. By comparing the impedance of the two coils, the defect may be identified. Due to the interplay between the magnetic fields, in this configuration, the eddy current probe has a greater sensitivity to defects that extend within, or parallel to, the planes of the coils.

Thus, an eddy current probe may be used in at least one of two configurations. These two configurations are each likely to detect defects in different planes, either aligned with the plane of a coil or angled relative to the plane of a coil. Thus, the typical method of using an eddy current probe requires the inspection sled to perform two passes over each inspection area; one pass with the eddy current probes in the driver pick-up mode and another pass with the eddy current probes in the impedance mode. This process is expensive and time consuming.

SUMMARY OF THE INVENTION

The disclosed and claimed concept provides for an eddy current probe testing apparatus structured to operate concurrently in both modes. In this configuration, the eddy current probe needs only one pass over a selected area to detect most defects. The eddy current probe is enabled to operate in both modes by use of a mode switching circuit. The mode switching circuit cycles rapidly between the two modes. The mode switching circuit may be controlled by a multiplexer, and the output therefrom may pass through a multiplexer. Further, there is an associated method of operating the eddy current probe testing apparatus in both modes concurrently.

BRIEF DESCRIPTION OF THE DRAWINGS

A further understanding of the invention can be gained from the following description of the preferred embodiments when read in conjunction with accompanying drawings in which.

DESCRIPTION OF THE PREFERRED EMBODIMENT

As used herein, "concurrently," as well as variations thereof, means near simultaneously. Any event that occurs with a frequency of greater than about 100 Hertz is a concurrent event.

As used herein, a "plane" includes a thin, i.e. a construct in three dimensional space, element or portion of another element.

It is understood that the apparatus and method disclosed herein may be used to inspect any surface and that the reference to use in a nuclear reactor is the preferred use.

Figure 1:
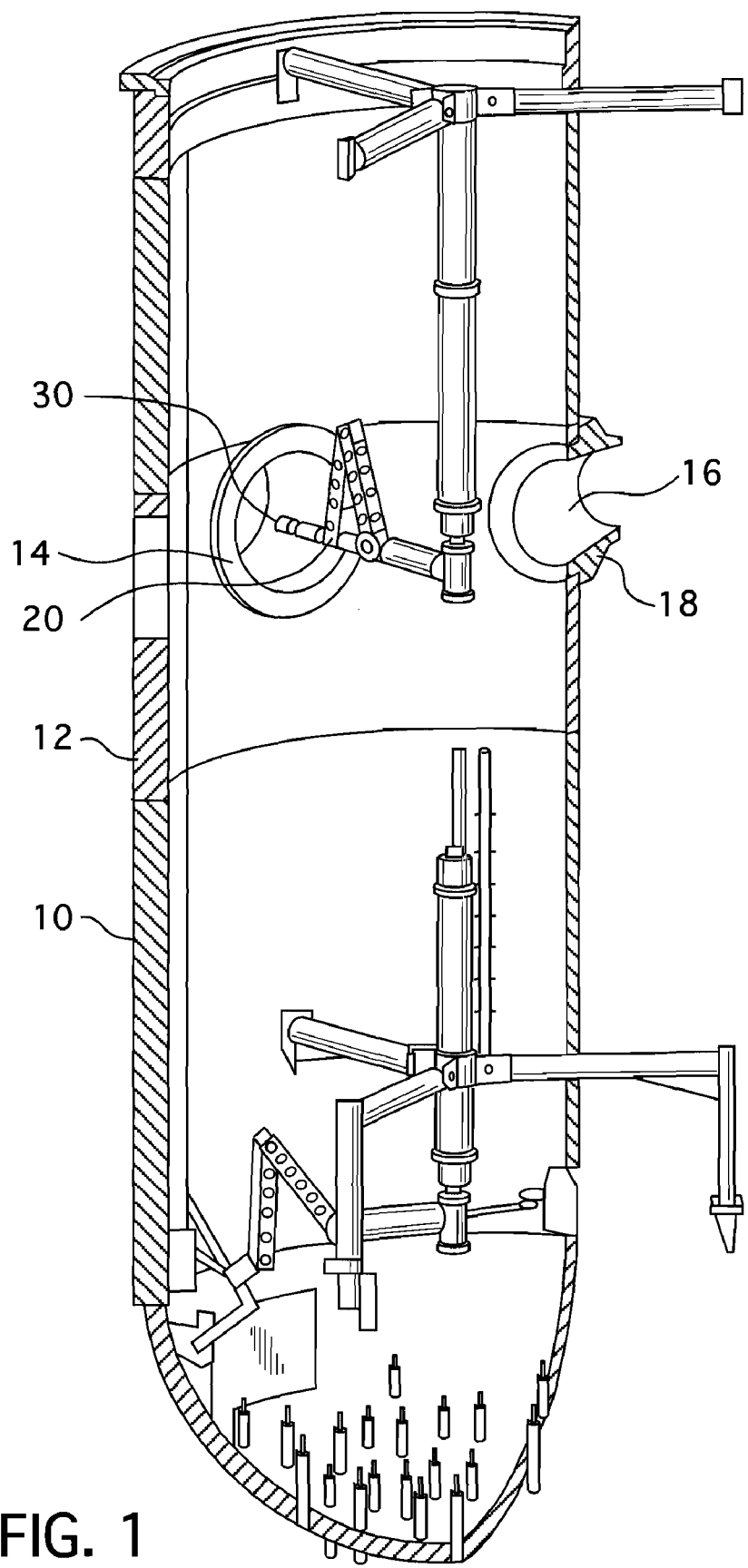
FIG. 1 is a cutaway isometric view of a nuclear reactor pressure vessel.

A nuclear reactor facility includes many components subjected to stress that must be inspected for defects. The nuclear reactor facility may include a plurality of components such as, but not limited to, a turbine assembly (not shown) and a pressure vessel 10 is shown in FIG. 1. The following description discusses the use of the eddy current probe testing apparatus in a nuclear reactor pressure vessel 10, but it is understood that the device recited in the claims below may be used in any component of the nuclear reactor facility. The nuclear reactor pressure vessel 10 encloses a nuclear fuel assembly (not shown), structured to contain nuclear fuel rods (not shown). The nuclear reactor pressure vessel 10 is a body 12 defining an enclosed space. The nuclear reactor pressure vessel 10 has a water inlet 14 and a water outlet 16. The nuclear reactor pressure vessel body 12, as well as the inlet 14 and outlet 16 each have a surface 18. Water is brought into the nuclear reactor pressure vessel 10 at the water inlet 14 and directed by one or more baffles (not shown) downwardly to the bottom of the nuclear fuel assembly. The water rises over the nuclear fuel assembly and is heated thereby. The hot water exits the nuclear reactor pressure vessel 10 via the water outlet 16.

As an operational nuclear reactor pressure vessel 10 is a hazardous environment, repair and inspection operations typically rely upon robotic, or other automated devices. Thus, the nuclear reactor pressure vessel 10 typically includes at least one robotic arm 20. The robotic arm 20 is articulated and structured to pivot/rotate so that the distal end of the robotic arm 20 may access a number of areas within the nuclear reactor pressure vessel 10. As many different types of inspections/repairs must be performed in a variety of locations within the nuclear reactor pressure vessel 10, the robotic arm 20 is adapted to support interchangeable end effectors 30. An end effector 30 is a device coupled to the distal end of the robotic arm 20 and which includes tools structured to perform a selected task. As the robotic arm 20 and end effector 30 are movable, the selected task, hereinafter an inspection, may be performed over an extended surface.

Figure 2:
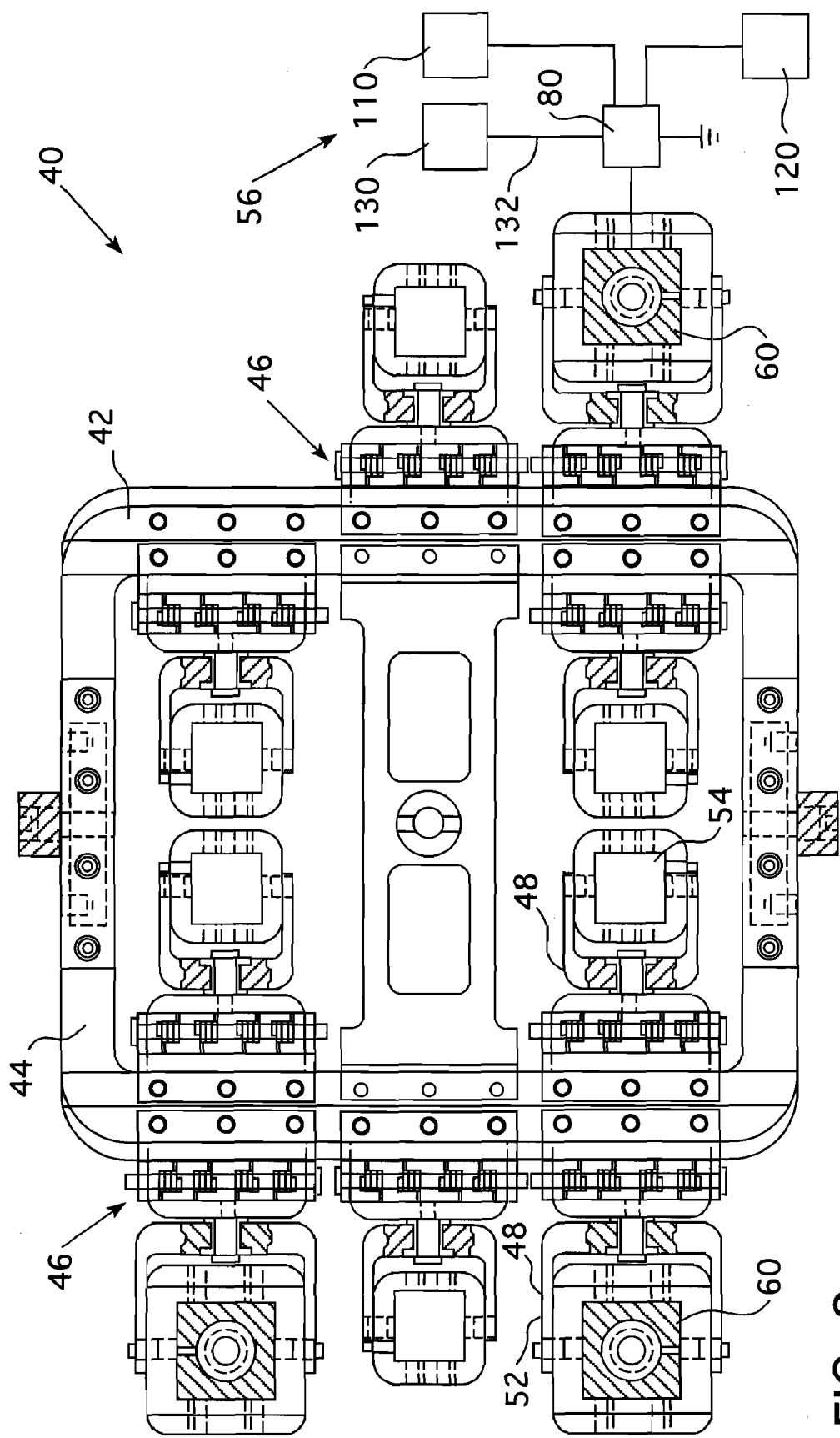
FIG. 2 is a top view of an end effector sled.
Figure 3:
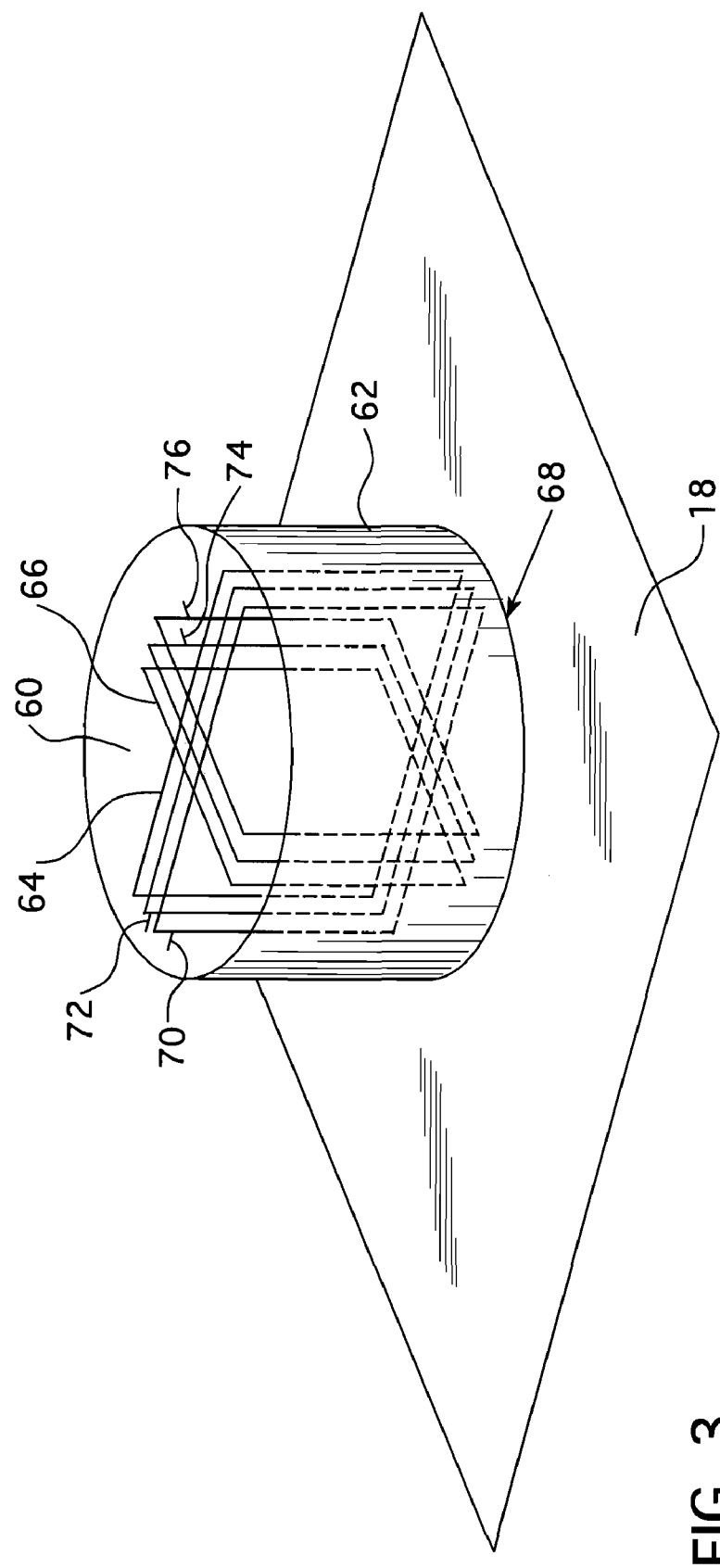
FIG. 3 is a schematic view of an eddy current probe.
Figure 4:
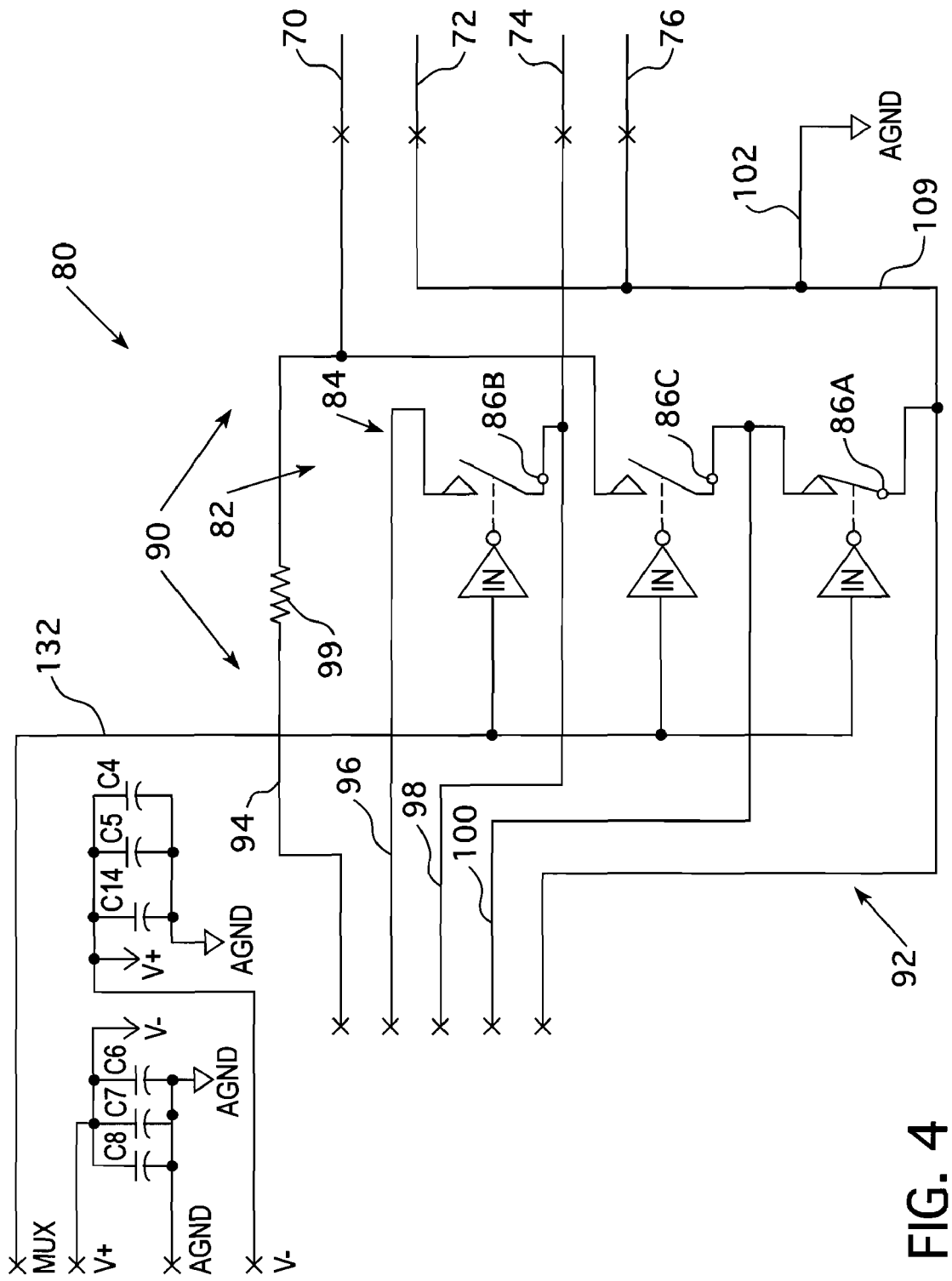
FIG. 4 is a circuit diagram of the mode switching circuit.

One type of end effector 30 is identified as a "sled" 40. A sled 40 is, typically, a frame upon which other devices may be mounted. For example, as shown in FIG. 2, an inspection sled 42 structured to inspect the water inlet 14 and the water outlet 16. The inspection sled 42, preferably, includes an articulated frame 44 having a plurality of couplings 46. The couplings 46 are structured to couple a mount 48 for a probe 50. As shown, the mounts 48 include at least one gimbal assembly 52 structured to support an eddy current probe 60. The at least one gimbal assembly 52 is pivotally coupled to the frame 44. In this configuration, the at least one gimbal assembly 52 is structured to support an eddy current probe 60 closely adjacent, or in contact with, the vessel body surface 18. The sled 40 may also support other devices such as, but not limited to, ultrasonic probes 54 and other test/inspection equipment.

The eddy current probe 60 is part of an eddy current probe testing apparatus 56. The eddy current probe testing apparatus 56 includes the robotic arm 20 and end effector sled 40 (both discussed above), a mode switching circuit 80, a ground bus 109, a signal producing device 110, an output device 120. The ground bus 109 is a grounded conductor. The signal producing device 110 is structured to produce at least one alternating current test signal. The signal producing device 110 is structured to control the characteristics of each signal produced, e.g. frequency, magnitude, phase, etc. The signal producing device 110 may include multiple outputs. A conductor assembly, or bus (not shown), disposed between, and in electrical communication with, the signal generator and the outputs may include one or more resistors (not shown). Such a resistor within the signal producing device 110, or a resistor external to the signal producing device 110 but in electrical communication with the signal producing device 110 output, can change the characteristics of the signal. Thus, if two separate signals are required, the signal producing device 110 may produce a single signal that is split and altered, or, the signal producing device 110 may include multiple signal generators (not shown) so that multiple original signals are produced. Each signal that is produced by the signal producing device 110 is an alternating current and may be communicated to an eddy current probe 60 via a conductor.

The output device 120 is structured to receive, and may record, an output signal from a eddy current probe 60. The output signal from a eddy current probe 60 is also electrical and may be communicated to the output device 120 via a conductor. The output device 120 may be structured to present the data in a form readable/viewable by humans. Such output devices 120 for eddy current probes 60 are known. It is noted that the signal producing device 110 and the output device 120, as well as other electronic components may be combined into a single housing.

The eddy current probe 60 is, preferably, a "+Point Probe." The eddy current probe 60 has a body 62 enclosing first and second coils 64, 66 of a conductive material, preferably copper wire (all shown schematically). The probe body 62 includes a generally flat inspection face 68. The inspection face 68 is structured to be placed adjacent to, or in contact with, the surface being inspected. The two coils 64, 66 preferably have a generally rectangular cross-section and are each disposed within a planar portion, or generally "a plane," within the probe body 62. Both coils 64, 66 extend in a plane that is generally perpendicular to the plane of the inspection face 68. Thus, during operation, the coils 64, 66 are typically disposed generally perpendicular to the plane of the surface being inspected, i.e. the vessel body surface 18. Each coil 64, 66 includes a first terminal and a second terminal. That is, there is a first coil first terminal 70, a first coil second terminal 72, a second coil first terminal 74, a second coil second terminal 76.

The mode switching circuit 80 includes a switch assembly 82 and a conductor assembly 90. The switch assembly 82 includes plurality of switches 84 and more preferably, a first switch 86A, a second switch 86B, and a third switch 86C. In the preferred embodiment, each switch 86A, 86B, 86C acts as a "single throw" switch structured to be either open or closed. Thus, each switch 86A, 86B, 86C is structured to provide selective electrical communication therethrough. That is, when a switch 86A, 86B, 86C is in an open position, a current may not flow through the switch 86A, 86B, 86C, and, when a switch 86A, 86B, 86C is in a closed position, a current may flow through the switch 86A, 86B, 86C. Each switch 86A, 86B, 86C is, preferably, an electrically controlled switch capable of changing states at a frequency of between about 1 and 1000 KHz.

The conductor assembly 90 includes a plurality of conductors 92, wherein selected conductors 92 are structured to provide electrical signals from the signal producing device 110 to the first coil 64 and the second coil 66, and, selected conductors 92 are structured to provide electrical signals from the first coil 64 and the second coil 66 to the output device 120. More specifically, the conductor assembly 90 includes a first input signal conductor 94, a second input signal conductor 96, a first output conductor 98, a second output conductor 100 and a ground conductor 102. The first input signal conductor 94 and the second input signal conductor 96 are coupled to, and in electronic communication with, the signal producing device 110. Thus, at least one signal may be provided to both the first input signal conductor 94 and the second input signal conductor 96. The first input signal conductor 94 is further coupled to, and in electronic communication with, the first coil first terminal 70. The ground conductor 102 is coupled to, and in electronic communication with, the ground bus 109. Further, the ground conductor 102 is coupled to, and in electronic communication with, both the first coil second terminal 72 and the second coil second terminal 76. The first output conductor 98 is coupled to, and in electronic communication with, the second coil first terminal 74. The first output conductor 98 and the second output conductor 100 are each coupled to the output device 120. As is known, the output device 120 stores and/or converts the signals received to a human readable form. It is noted that the first input signal conductor 94 may include a resistor 99 structured to balance the impedance between the two coils 64, 66 when in the impedance mode.

The first switch 86A is coupled to, and structured to provide selective electrical communication between, the ground bus 109 and the second output conductor 100. The second switch 86B is coupled to, and structured to provide selective electrical communication between, the second input signal conductor 96 and the first output conductor 98. The third switch 86C is coupled to, and structured to provide selective electrical communication between, the first input signal conductor 94 and said second output conductor 100. It is noted that the first and third switches 86A, 86C may be combined into a changeover switch (not shown).

With this configuration of conductors 92 and switches 84, the switch assembly 82, and therefore the eddy current probe 60, may be switched between a first configuration, wherein the eddy current probe 60 acts in a driver pick-up mode, and a second configuration, wherein the eddy current probe 60 acts in an impedance mode. That is, in the first configuration, the first switch 86A is closed, thereby grounding the second output conductor 100, and second and third switches 86B, 86C are open. Thus, the first input signal conductor 94 is coupled to the first coil first terminal 70 and the first coil 64 receives a signal from the signal producing device 110. As the second switch 86B is open, there is not a closed connection between the second input signal conductor 96 and the first output conductor 98. Thus, there is not a connection between the signal producing device 110 and the second coil 66. In this configuration, the first coil 64 receives a signal and the second coil 66 is grounded. This configuration conforms to the configuration for an eddy current probe 60 in the driver pick-up mode.

In the second configuration of the switch assembly 82, the first switch 86A is moved to the open position and the second and third switches 86B, 86C are moved to the closed position. Thus, the second input signal conductor 96, as well as the second coil first terminal 74, are coupled to, and in electrical communication with, the first output conductor 98 via the second switch 86B. Further, the first input signal conductor 94, as well as the first coil first terminal 70, are coupled to, and in electrical communication with, the second output conductor 100 via the third switch 86B. This configuration conforms to the configuration for an eddy current probe 60 in the impedance mode.

The switch assembly 82 is structured to move rapidly between the two identified configurations. The speed at which the switch assembly 82 changes configurations is related to both the speed at which the inspection sled 42 moves over the body surface 18 (discussed below) and the frequency of the eddy current test signal. A table indicating possible test signal frequencies and associated switch frequencies is set forth below.

| Eddy Current Test Freq. KHz | Maximum switch Freq KHz |
|---|---|
| 10 | 1 |
| 100 | 10 |
| 200 | 20 |
| 500 | 49 |
| 1,000 | 96 |
| 10,000 | 714 |

Preferably, the switch assembly 82 moves between these configurations at a frequency between about 1 and 714 KHz, and more preferably at about one tenth the test signal frequency. Thus, the eddy current probe 60 is structured to acts in both modes concurrently.

The switch assembly 82 may be controlled by a multiplexer 130 (shown schematically). The multiplexer 130 is structured to create a switch control signal and to detect the configuration of the switch assembly 82. The multiplexer 130 includes a multiplexer input conductor 132 that extends, and provides electrical communication, between the multiplexer 130 and each switch 86A, 86B, 86C in the switch assembly 82. The switch control signal causes the switch assembly 82 to move between the configurations discussed above. As noted above, the output signal from the eddy current probe 60 may also pass through a multiplexer 130.

Accordingly, the disclosed eddy current probe testing apparatus 56 may be used to perform a single pass inspection of a substrate. That is, rather than moving the inspection sled 42 over an area being inspected twice, once in the driver pick-up mode and again in the impedance mode, the inspection sled 42 needs to pass over an area only once. Thus, the eddy current probe testing apparatus 56 may be used in a method including the steps of positioning 200 an end effector sled 40, having at least one eddy current probe 60, within the nuclear reactor pressure vessel 10 with the at least one eddy current probe 60 disposed adjacent the nuclear reactor pressure vessel body 12, and, performing 202 an inspection of the nuclear reactor pressure vessel body 12 using the at least one eddy current probe 60, the at least one eddy current probe 60 acting concurrently in the driver pick-up mode and the impedance mode. The step of performing 202 an inspection includes the step of moving 204 the end effector inspection sled 42 over the body surface 18. Preferably, the end effector inspection sled 42 moves over the body surface 18 at a speed of between about 0.25 and 2.5 meters/second, and more preferably about 1.0 meters/second. While specific embodiments of the invention have been described in detail, it will be appreciated by those skilled in the art that various modifications and alternatives to those details could be developed in light of the overall teachings of the disclosure. Accordingly, the particular embodiments disclosed are meant to be illustrative only and not limiting as to the scope of the invention which is to be given the breath of the appended claims and any and all equivalents thereof.

What is claimed is:

1. A mode switching circuit structured to operate with an eddy current probe testing apparatus, said eddy current probe testing apparatus having a signal producing device, an output device, a ground bus, and an eddy current probe, said signal producing device structured to produce at least one test signal having a frequency, said output device structured to convert at least one output signal to a displayable format, said eddy current probe structured to operate in an first mode and a second mode to detect defects in a body having a surface, said eddy current probe having a first coil and a second coil, said first coil extending in a plane substantially perpendicular to said body surface, said second coil extending in a in a plane substantially perpendicular to said body surface and to said first coil, said first coil having a first terminal and a second terminal, said second coil having a first terminal and a second terminal, said mode switching circuit comprising:
a switch assembly having a plurality of switches;
a conductor assembly having a plurality of conductors, wherein selected conductors are structured to provide electrical signals from said signal producing device to said first coil and said second coil, and, selected conductors are structured to provide electrical signals from said first coil and said second coil to said output device;
wherein selected conductors of said plurality of conductors are coupled to, and in electronic communication with, at least one switch of said plurality of switches, each said switch further coupled to, and in electrical communication with at least one of said first coil and said second coil; and
wherein said switch assembly is structured to have said plurality of switches rapidly move between a first configuration, wherein said eddy current probe acts in a driver pick-up mode, and a second configuration, wherein said eddy current probe acts in an impedance mode, whereby said eddy current probe acts in both modes concurrently.

2. The mode switching circuit of claim 1 wherein:
said conductor assembly includes a first input signal conductor, a second input signal conductor, a first output conductor, a second output conductor and a ground conductor;
said switch assembly having at least a first, a second, and a third switch structured to provide selective electrical communication through said switch;
said first input signal conductor and said second input signal conductor coupled to, and in electronic communication with, said signal producing device whereby at least one signal is provided to both said first input signal conductor and said second input signal conductor;
said first input signal conductor coupled to, and in electronic communication with, said first coil first terminal;
said ground conductor coupled to, and in electronic communication with, said ground bus;
said ground conductor coupled to, and in electronic communication with, said first coil second terminal and said second coil second terminal;
said first output conductor coupled to, and in electronic communication with, said second coil first terminal;
said first switch coupled to, and structured to provide selective electrical communication between, said ground bus and said second output conductor;
said second switch coupled to, and structured to provide selective electrical communication between, said second input signal conductor and said first output conductor; and
said third switch coupled to, and structured to provide selective electrical communication between, said first input signal conductor and said second output conductor.

3. The mode switching circuit of claim 1 wherein said switch assembly is structured to move between said first configuration and said second configuration at a frequency between about 1 and 714 KHz.

4. The mode switching circuit of claim 3 wherein said switch assembly is structured to move between said first configuration and said second configuration at a frequency about one tenth the frequency of said test signal.

5. The mode switching circuit of claim 1 further comprising:
a multiplexer structured to create a switch control signal and detect the configuration of said switch assembly;
a multiplexer input conductor extending, and providing electrical communication, between said multiplexer and each switch in said switch assembly;
whereby said multiplexer controls the configuration of said switch assembly and detects the state of said switch assembly.

6. A mode switching circuit structured to operate with an eddy current probe testing apparatus, said eddy current probe testing apparatus having a signal producing device, an output device, a ground bus, and an eddy current probe, said signal producing device structured to produce at least one test signal, said output device structured to convert at least one output signal to a displayable format, said eddy current probe structured to operate in an first mode and a second mode to detect defects in a body having a surface, said eddy current probe having a first coil and a second coil, said first coil extending in a plane substantially perpendicular to said body surface, said second coil extending in a in a plane substantially perpendicular to said body surface and to said first coil, said first coil having a first terminal and a second terminal, said second coil having a first terminal and a second terminal, said mode switching circuit comprising:
a first input signal conductor, a second input signal conductor, a first output conductor, a second output conductor, and a switch assembly;
said first input signal conductor and said second input signal conductor coupled to, and in electronic communication with, said signal producing device whereby a signal is provided to both said first input signal conductor and said second input signal conductor;
said first input signal conductor coupled to, and in electronic communication with, said first coil first terminal;
said ground conductor coupled to, and in electronic communication with, said ground bus;
said ground conductor coupled to, and in electronic communication with, said first coil second terminal and said second coil second terminal;
said first output conductor coupled to, and in electronic communication with, said second coil first terminal;
said switch assembly having at least a first, a second, and a third switch, each said switch structured to move between an open position, wherein there is no electrical communication through the switch, and a closed position, wherein there is electrical communication through the switch, thereby providing selective electrical communication through said switch;
said first switch coupled to, and structured to provide selective electrical communication between, said ground bus and said second output conductor;
said second switch coupled to, and structured to provide selective electrical communication between, said second input signal conductor and said first output conductor; and
said third switch coupled to, and structured to provide selective electrical communication between, said first input signal conductor and said second output conductor.

7. The mode switching circuit of claim 6 wherein said switch assembly is structured to move between a first configuration, wherein said first switch is closed and said second and third switches are open, and a second configuration, wherein said first switch is open and said second and third switches are closed, at a frequency between about 1 and 714 Hertz.

8. The mode switching circuit of claim 7 wherein said switch assembly is structured to move between said first configuration and said second configuration at a frequency about one tenth the frequency of said test signal.

9. An eddy current probe testing apparatus for a nuclear reactor pressure vessel, said nuclear reactor pressure vessel being a body with a surface, said eddy current probe testing apparatus comprising:
a robotic arm disposed within said nuclear reactor pressure vessel, said robotic arm having an end effector sled;
said end effector sled having a body with a plurality of couplings;
at least one eddy current probe structured to operate in an first mode and a second mode to detect defects in a body having a surface, said eddy current probe having a first coil and a second coil, said first coil extending in a plane substantially perpendicular to a portion of said body surface, said second coil extending in a in a plane substantially perpendicular to said body surface and to said first coil;
said first coil having a first terminal and a second terminal;
said second coil having a first terminal and a second terminal;
a signal producing device structured to produce at least one test signal for said at least one eddy current probe;
an output device structured to convert at least one output signal from said at least one eddy current probe to a displayable format;
a ground bus;
a mode switching circuit having a switch assembly and a conductor assembly;
said switch assembly having a plurality of switches;
said conductor assembly having a plurality of conductors, wherein selected conductors are structured to provide electrical signals from said signal producing device to said first coil and said second coil, and, selected conductors are structured to provide electrical signals from said first coil and said second coil to said output device;
wherein selected conductors of said plurality of conductors are coupled to, and in electronic communication with, at least one switch of said plurality of switches, each said switch further coupled to, and in electrical communication with at least one of said first coil and said second coil; and
wherein said switch assembly is structured to have said plurality of switches rapidly move between a first configuration, wherein said eddy current probe acts in a driver pick-up mode, and a second configuration, wherein said eddy current probe acts in an impedance mode, whereby said eddy current probe acts in both modes concurrently.

10. The eddy current probe testing apparatus of claim 9 wherein:
said conductor assembly includes a first input signal conductor, a second input signal conductor, a first output conductor, a second output conductor;
said switch assembly having at least a first, a second, and a third switch structured to provide selective electrical communication through said switch;
said first input signal conductor and said second input signal conductor coupled to, and in electronic communication with, said signal producing device whereby a signal is provided to both said first input signal conductor and said second input signal conductor;
said first input signal conductor coupled to, and in electronic communication with, said first coil first terminal;
said ground conductor coupled to, and in electronic communication with, said ground bus;
said ground conductor coupled to, and in electronic communication with, said first coil second terminal and said second coil second terminal;
said first output conductor coupled to, and in electronic communication with, said second coil first terminal;
said first switch coupled to, and structured to provide selective electrical communication between, said ground bus and said second output conductor;
said second switch coupled to, and structured to provide selective electrical communication between, said second input signal conductor and said first output conductor; and
said third switch coupled to, and structured to provide selective electrical communication between, said first input signal conductor and said second output conductor.

11. The eddy current probe testing apparatus of claim 9 wherein said switch assembly is structured to move between said first configuration and said second configuration at a frequency between about 1 and 714 KHz.

12. The eddy current probe testing apparatus of claim 11 wherein said switch assembly is structured to move between said first configuration and said second configuration at a frequency about one tenth the frequency of said test signal.

13. The eddy current probe testing apparatus of claim 9 further comprising:
a multiplexer structured to create a switch control signal and detect the configuration of said switch assembly;
a multiplexer input conductor extending, and providing electrical communication, between said multiplexer and each switch in said switch assembly;
whereby said multiplexer controls the configuration of said switch assembly and detects the state of said switch assembly.

14. The eddy current probe testing apparatus of claim 9 wherein:
said end effector sled includes at least one gimbal assembly structured to support one said at least one eddy current probe; and
said at least one gimbal assembly coupled to said end effector sled body.

* * * * *